United States Patent
Huet

(10) Patent No.: US 6,663,604 B1
(45) Date of Patent: Dec. 16, 2003

(54) ANTI-STICK DEVICE FOR THE SAFE HANDLING OF AN INJECTION NEEDLE

(75) Inventor: Jean-Max Huet, Clichy (FR)

(73) Assignee: Vygon, Ecouen (FR)

( * ) Notice: Subject to any disclaimer, the term of this patent is extended or adjusted under 35 U.S.C. 154(b) by 325 days.

(21) Appl. No.: 09/602,389

(22) Filed: Jun. 22, 2000

(30) Foreign Application Priority Data

Jan. 12, 2000 (FR) .............................................. 00 0330

(51) Int. Cl.⁷ ................................................. A61M 5/00
(52) U.S. Cl. ....................................................... 604/263
(58) Field of Search ............................. 604/263, 93.01, 604/198, 177, 192, 110; 128/919

(56) References Cited

U.S. PATENT DOCUMENTS

| | | | | |
|---|---|---|---|---|
| 4,717,386 A | * | 1/1988 | Simmons | 604/192 |
| 4,820,282 A | * | 4/1989 | Hogan | 128/DIG. 26 |
| 4,852,844 A | * | 8/1989 | Villaveces | 248/314 |
| 4,981,476 A | * | 1/1991 | Aichlmayr et al. | 206/365 |
| 5,125,912 A | * | 6/1992 | Kinnel | 206/365 |
| 5,156,426 A | * | 10/1992 | Graves | 294/1.1 |
| 5,279,577 A | * | 1/1994 | Collett | 129/919 |
| 5,322,517 A | * | 6/1994 | Sircom et al. | 604/198 |
| 5,531,704 A | | 7/1996 | Knotek | |
| 5,702,369 A | * | 12/1997 | Mercereau | 604/110 |
| 5,951,522 A | | 9/1999 | Rosato et al. | |
| 6,379,332 B1 | * | 4/2002 | Van Landuyt | 604/164.07 |

* cited by examiner

Primary Examiner—Daniel Robinson
(74) Attorney, Agent, or Firm—Levine & Mandelbaum

(57) ABSTRACT

Anti-stick device for the safe handling of a needle for transcutaneous injection, this device being formed by two plates (F,D) arranged one above the other and fixed to one another by links (B,C,E,A) such that the device can change from a configuration in which the two plates are pressed against one another to a configuration in which they are spaced apart from one another, providing between them a space surrounded by the said links, and into which the part (17) of the needle which penetrated the skin can be retracted as it is removed.

13 Claims, 3 Drawing Sheets

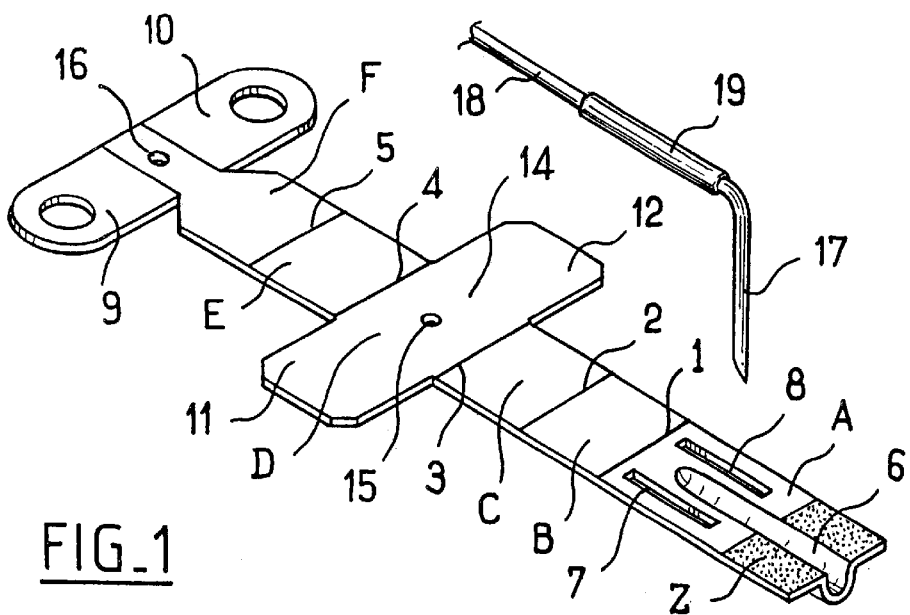
FIG.1
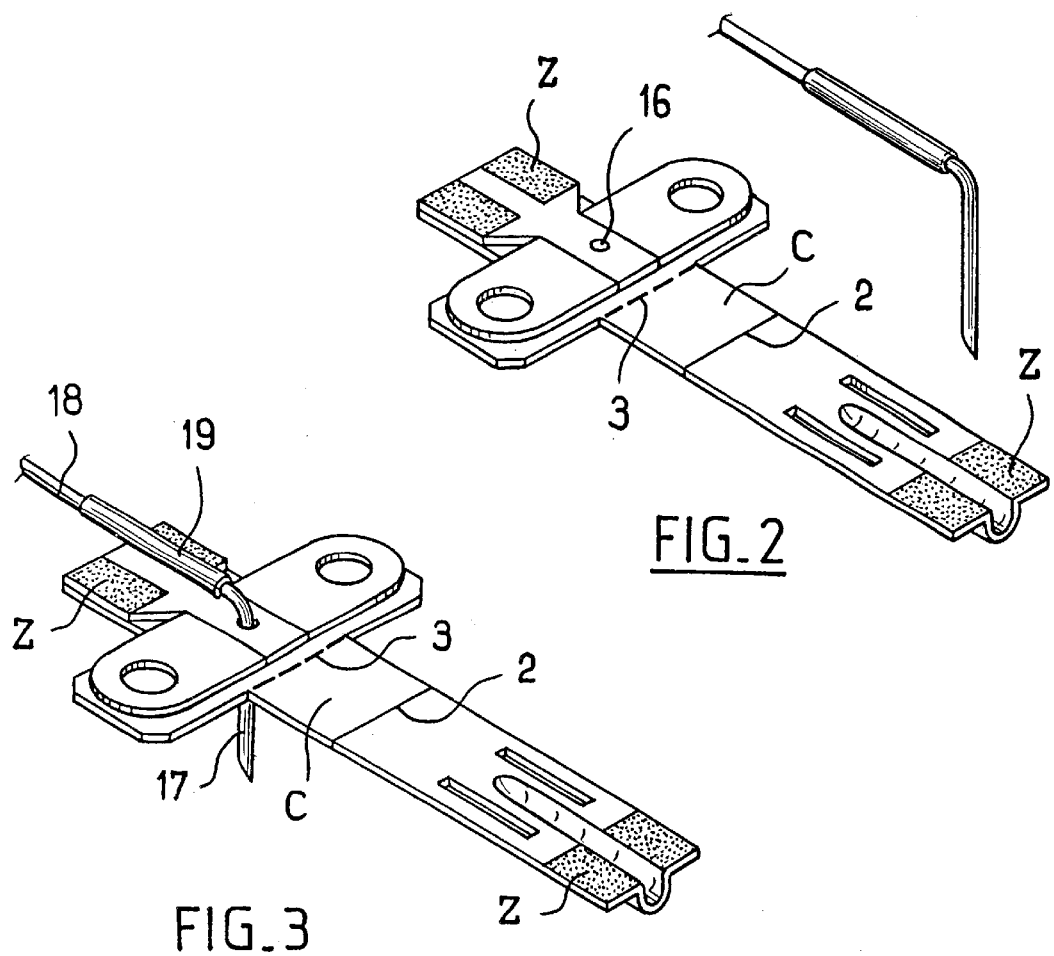
FIG.2
FIG.3

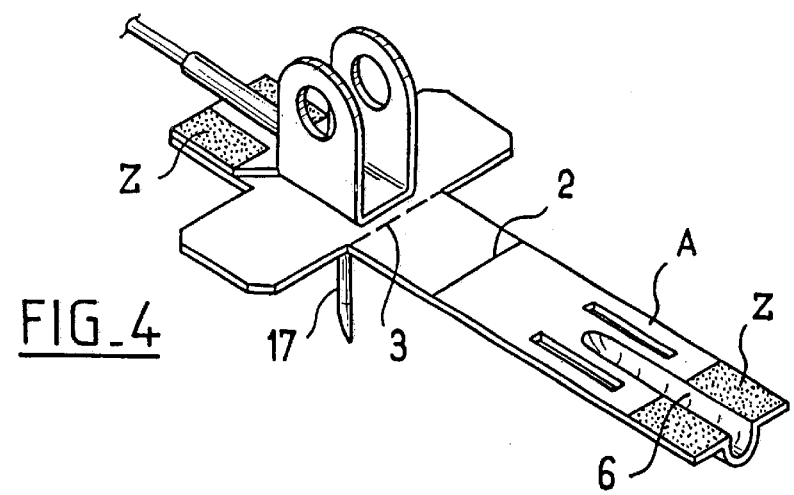
FIG_4
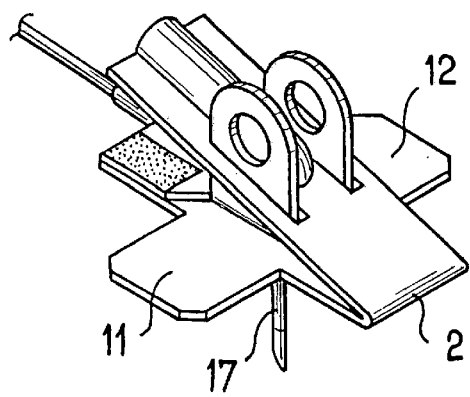
FIG_5
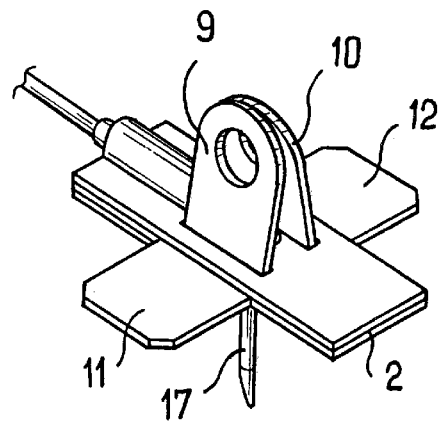
FIG_6
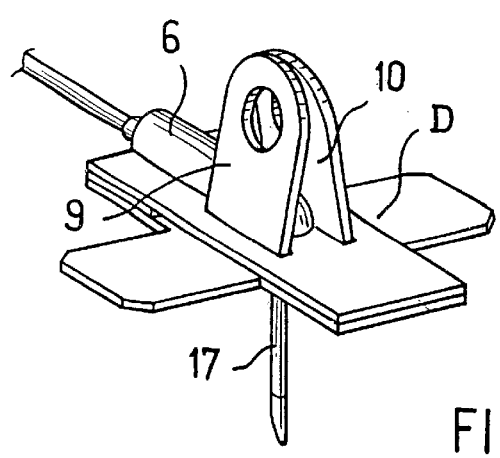
FIG_7

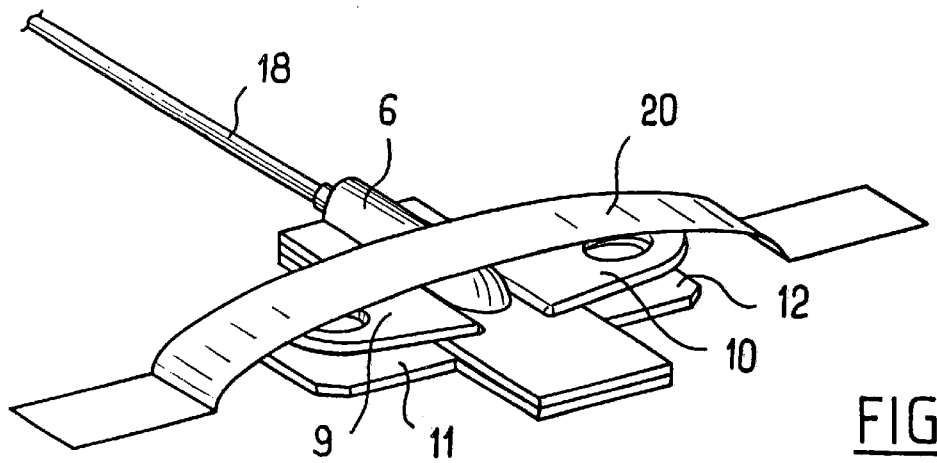
FIG_8
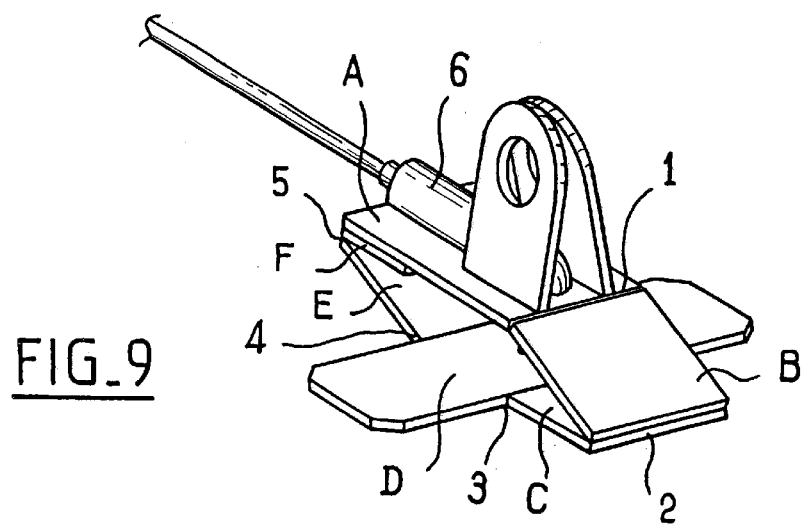
FIG_9
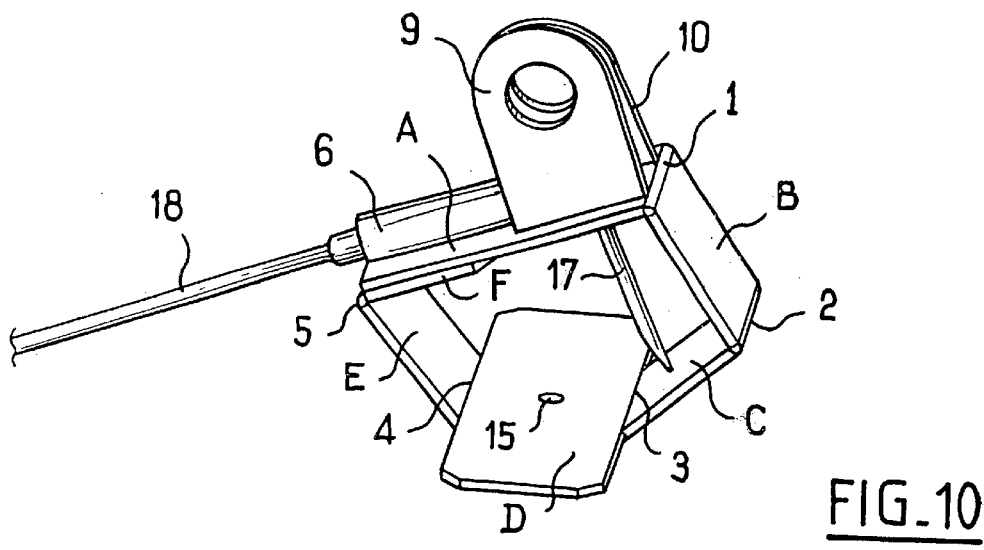
FIG_10

ANTI-STICK DEVICE FOR THE SAFE HANDLING OF AN INJECTION NEEDLE

BACKGROUND OF THE INVENTION

Field of the Invention

The invention relates to an anti-stick device for the safe handling of an injection needle in the medical sector.

SUMMARY OF THE INVENTION

It is an object of the invention to provide a device which is relatively inexpensive, is easy to manufacture and is suitable for one-time use.

The device according to the invention is formed by two plates arranged one above the other and fixed to one another by links such that the device can change from a configuration in which the two plates are pressed against one another to a configuration in which they are spaced apart from one another, providing between them a space surrounded by the said links, one of the plates being suitable for carrying the needle and the other plate or base plate being suitable for being pressed against the skin around the point of injection and having a hole to allow through the part of the needle which is to penetrate the skin, and the said space being sufficient to ensure that, during the removal of the needle from the skin and from the said hole, the said needle part can be retracted into the said space as it is removed.

In preferred embodiments, the device has one or more of the following additional characteristics:

- the links between the two plates are formed by panels articulated by fold lines;
- the device has the means to make it easier to hold in the hand in order to push in the needle and move the two plates apart;
- the base plate bears lateral wings which allow it to be pressed more easily against the skin;
- the needle-carrying plate bears two lugs, which can be raised to allow the device to be gripped;
- the needle-carrying plate has a hole to allow the said needle part to pass through;
- the needle-carrying plate has a recess to accept one branch of the needle, which forms an elbow with the said needle part.

BRIEF DESCRIPTION OF THE DRAWINGS

One embodiment of a device in accordance with the invention, given essentially by way of non-limitative example, will be described below with reference to the figures of the attached drawing, in which:

FIG. 1 is a view of a flat blank to be made up to form the device according to the invention;

FIGS. 2 to 6 represent successive phases of the making up of the blank in FIG. 1;

FIGS. 7 and 8 represent two phases of the operation for placing the device and

FIGS. 9 and 10 represent two phases of the operation of removing the needle from the skin.

DETAILED DESCRIPTION OF THE PREFERRED EMBODIMENT

The device represented in the figures is formed from a single wall, for example a semi-rigid sheet cut from a blank of synthetic material.

This single wall has weakening lines (1–5) which form 5 parallel fold lines that divide the wall into 6 successive panels (A,B,C,D,E,F); panels (F) and (D) respectively form a needle-carrying plate and a base plate; panels (B), (C) and (E) form connecting panels between these two plates, and panel (A) forms a panel suitable for fixing to the needle-carrying plate (F) by adhesive bonding or welding.

One (A) of the end panels of the series of panels laid flat has two elongate parallel apertures (7,8) and the other panel (F) of the series of panels laid flat has two lateral lugs (9,10), which can be folded at right angles to the panel, facing one another (FIG. 4), and can be introduced into the apertures in panel (A) when these two panels are pressed against one another (FIG. 5); these two panels are kept together by adhesive bonding or welding. In FIGS. 1 to 5, the zones (Z) of these panels which are fixed to one another in this way have been indicated by stippling.

In FIG. 2, the end section (F) has been folded about the line (5) but the other end section (A) has not yet been folded.

In FIG. 5, the end section (A) is in the process of being folded about the line (2) and has not yet been folded down completely against the central section (D); the two lugs (9,10) have been engaged in the apertures (7,8).

In the embodiment shown, the central section has two lateral wings (11,12) arranged such that the lugs (9,10) of the end section (F) come to rest against these wings when this section is folded down against the central section, and such that the thickness of the central part (13) of the end section (F) is added to the thickness of the central part (14) of the central section (D).

These two central parts (13,14) of the sections (D) and (F) are provided with perforations (15,16) which allow the branch (17) of the needle which is to penetrate the body to pass through, and this double thickness helps to provide good support for the needle during penetration.

In the case shown (FIG. 1), this needle is elbowed and has a distal branch (17) for piercing and a proximal branch (18) for supply; a sheath section (19) on the proximal branch, close to the elbow, makes it easier to grasp to place it in the device.

The needle is put in place and held in the device by introducing its piercing distal branch (17) into the superimposed perforations (15,16) (FIG. 3) and folding the end panel (A) over onto the proximal branch (18) of the needle (FIGS. 5 and 6). It is advantageous if this end panel (A) has, on the face which will be turned towards the needle, a recess (6) in which the sheath section (19) and the elbow of the needle are accommodated.

The placing of the device is effected by holding the device by the lugs (9,10) (FIG. 7) and pushing it so as to pierce the skin by means of the distal branch (17) of the needle until the central panel (D) of the device is pressed against the skin; the two lugs (9,10) are then folded over flat onto the lateral wings (11,12) and an adhesive strip (20) is pressed onto the device thus flattened and onto the skin to hold the needle and the device (FIG. 8) in place.

To extract the needle, the operator removes the adhesive strip, raises the lugs (9,10) and pulls them towards him with one hand to extract the needle from the skin while keeping the central section (D) pressed against the skin (FIG. 9) with his other hand. The device deforms due to the fold lines during the process of extraction such that the piercing branch (17) of the needle remains continuously within the pentagon formed by the panels (A) to (E) of the device (FIG. 10).

The invention is not limited to this embodiment. In particular, it is not limited to any particular means of providing the device with the ability for deformation (flexible wall, articulated wall, fold lines etc.).

In most cases, combined use will be made of the flexibility of the panels and of a number of fold lines; thus, the folds 3 and 4 can be due to fold lines or to an ability of the central panel (D) for deformation, which in this case forms a single panel with panels (C) and (E).

What is claimed is:

1. An anti-stick device for the safe handling of a needle for transcutaneous injection, said device comprising a base plate and a needle-carrying plate arranged one above the other and connected to one another by links such that the device can change from a configuration in which the plates are pressed against one another to a configuration in which they are spaced apart from one another, the needle-carrying plate being suitable for carrying the needle and the base plate being suitable for being pressed against the skin around the point of injection and having a hole for passing a part of the needle which is to penetrate the skin, said space being sufficient to ensure that, during the removal of the needle from the skin and from said hole, said needle part can be retracted into said space as it is removed, said device comprising a single wall which has fold lines that divide the wall into a plurality of sections comprising a central section, which forms said base plate, a section which forms said needle-carrying plate, and end section, and a plurality of linking sections which form said links, the end section comprising two elongate perforations and the needle-carrying section comprising two lateral lugs capable of being folded at right angles to the needle-carrying section and positioned facing one another for being introduced into said perforations when the needle-carrying section and end section are pressed against one another.

2. A device according to claim 1, having means to make it easier to hold in the hand in order to push in the needle and move the two plates apart.

3. Device according to claim 2, in which the needle-carrying plate is provided with gripping means which allow the device to be gripped in order to push the needle into the skin and move the two plates closer together or further apart.

4. Device according to one of claim 1, in which the needle-carrying plate comprises two lugs, which can be raised to allow the device to be gripped.

5. Device according to claim 1, in which the end wall has a recess to accept one branch of the needle, which forms an elbow with said needle part.

6. Device according to claim 1, of which the base plate has two lateral wings.

7. Device according to claim 1, in which the base plate and the needle-carrying plate have holes to allow said needle part to pass through.

8. Device according to claim 1, in which said wall is a semi-rigid sheet cut from a blank of synthetic material.

9. An anti-stick device for the safe handling of an elbowed needle having a piercing distal branch and a supplying proximal branch, for transcutaneous injection;

said device comprising a single semi-rigid and foldable wall having fold lines for dividing the wall into a base wall section, a needle carrying wall section and an end wall section;

said base wall section and said needle carrying wall section having respective perforations through which the piercing branch of the needle can pass;

said wall being foldable into one configuration in which said base wall section and said needle carrying wall section are pressed against one another with their respective perforations superimposed for receiving the piercing branch of the needle, and in which the end wall section may be folded over onto the proximal branch of the needle and fixed to the needle-carrying wall section;

said wall also being foldable into another configuration in which said base wall section and said needle carrying wall section are in spaced relationship for receiving the piercing branch of the needle therebetween when the needle is removed from the skin;

said needle-carrying wall section comprising two lateral foldable lugs which may be raised to form a grip for enabling the piercing branch of the needle to be pushed into the skin or for extracting said piercing branch from the skin.

10. A device according to claim 9 wherein the end wall section has a recess for receiving said proximal branch of the needle.

11. A device according to claim 9 wherein the end wall section has two elongate perforations through which said lugs may be introduced.

12. A device according to claim 9 wherein said base wall section has two lateral wings.

13. A device according to claim 9 wherein the wall is cut from a blank of synthetic material.

* * * * *